US012734280B2

(12) United States Patent
Van Veldhuizen et al.

(10) Patent No.: US 12,734,280 B2
(45) Date of Patent: Sep. 15, 2026

(54) EXPRESSION ASSEMBLY FOR A BREAST PUMP AND A BREAST PUMP HAVING THE EXPRESSION ASSEMBLY

(71) Applicant: KONINKLIJKE PHILIPS N.V., Eindhoven (NL)

(72) Inventors: Gijsbert Hendrik Van Veldhuizen, Groningen (NL); Camiel Gubbels, Nederweert-Eind (NL); Coen Petrus Martinus Claassen, Lommel (BE); Christoph Dobrusskin, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 518 days.

(21) Appl. No.: 18/276,485

(22) PCT Filed: Mar. 14, 2022

(86) PCT No.: PCT/EP2022/056421
§ 371 (c)(1),
(2) Date: Aug. 9, 2023

(87) PCT Pub. No.: WO2022/194721
PCT Pub. Date: Sep. 22, 2022

(65) Prior Publication Data

US 2024/0115778 A1 Apr. 11, 2024

(30) Foreign Application Priority Data

Mar. 16, 2021 (EP) .................................... 21162874

(51) Int. Cl.
*A61M 1/06* (2006.01)

(52) U.S. Cl.
CPC ............ *A61M 1/066* (2014.02); *A61M 1/062* (2014.02); *A61M 1/064* (2014.02); *A61M 1/067* (2021.05); *A61M 1/06935* (2021.05); *A61M 2209/088* (2013.01)

(58) Field of Classification Search
CPC ...... A61M 1/066; A61M 1/064; A61M 1/067; A61M 1/06935; A61M 1/062; A61M 2209/088
See application file for complete search history.

(56) References Cited

U.S. PATENT DOCUMENTS

| | | | |
|---|---|---|---|
| 8,568,350 | B2 | 10/2013 | Schlienger et al. |
| 10,335,525 | B2 | 7/2019 | Felber et al. |
| 10,702,640 | B2 | 7/2020 | Alvarez et al. |
| 2005/0154349 | A1 | 7/2005 | Renz et al. |
| 2011/0071466 | A1 | 3/2011 | Silver et al. |
| 2016/0000982 | A1 | 1/2016 | Alvarez et al. |

(Continued)

OTHER PUBLICATIONS

International Search report and Written Opinion of PCT/EP2022/056421, dated Jun. 24, 2022.

*Primary Examiner* — Tasnim Mehjabin Ahmed

(57) ABSTRACT

An expression assembly for breast pump comprises a diaphragm, a cover over the diaphragm to define a sealed space between them, and a breast shield to which the cover and diaphragm are coupled. The diaphragm defines a cavity having an open end for receiving a nipple of a user and a closed end. The open end is angled back at the top to cover more of the top of the breast. This enables the diaphragm to provide better stimulation of the breast as well reducing leakage.

14 Claims, 11 Drawing Sheets

(56) References Cited

U.S. PATENT DOCUMENTS

| | | | | |
|---|---|---|---|---|
| 2018/0021491 | A1 | 1/2018 | Rigert et al. | |
| 2018/0078687 | A1 | 3/2018 | Alvarez et al. | |
| 2018/0154055 | A1 * | 6/2018 | Alvarez ................ | A61M 1/064 |
| 2020/0016307 | A1 | 1/2020 | Edelman | |
| 2024/0115778 | A1 | 4/2024 | Van Veldhuizen | |
| 2024/0293602 | A1 * | 9/2024 | Van Veldhuizen .... | A61M 1/066 |

* cited by examiner

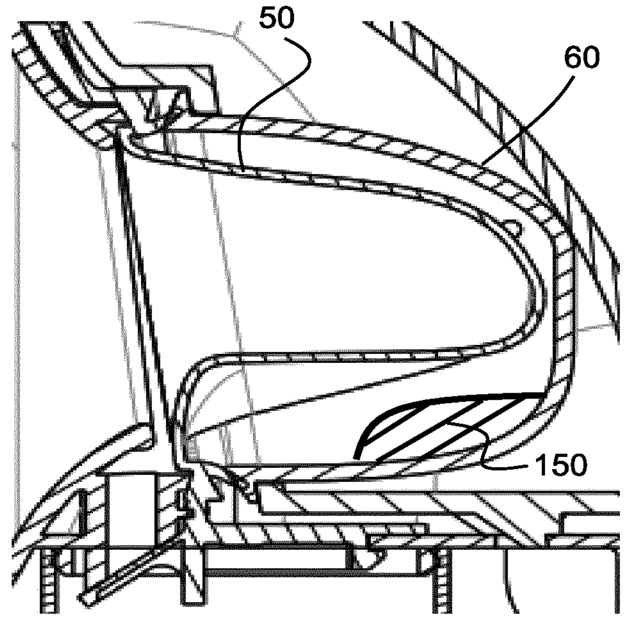
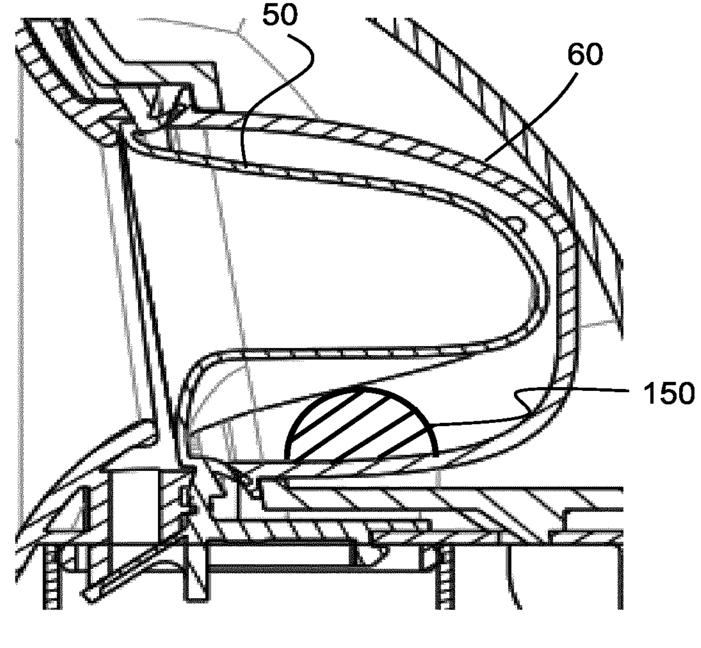
FIG. 9

EXPRESSION ASSEMBLY FOR A BREAST PUMP AND A BREAST PUMP HAVING THE EXPRESSION ASSEMBLY

CROSS-REFERENCE TO PRIOR APPLICATIONS

This application is the U.S. National Phase application under 35 U.S.C. § 371 of International Application No. PCT/EP2022/056421, filed on Mar. 14, 2022, which claims the benefit of European Patent Application No. 21162874.8, filed on Mar. 16, 2021. These applications are hereby incorporated by reference herein.

FIELD OF THE INVENTION

This invention relates to breast pumps, and in particular to breast pumps which use a diaphragm between the pressure source (e.g. vacuum pump) and the breast.

BACKGROUND OF THE INVENTION

Breast pumps are used by breast feeding women to extract milk from their breast such that the extracted milk can be fed to their babies at a later time.

It is well known that best nutrition for babies is breast milk. The world health organization (WHO) recommends to breast feed babies for at least one year, preferably longer. However, mothers often go back to work after only several weeks or months. To provide the best nutrition to their babies, mothers may then express milk using a breast pump. The expressed milk can be stored and given to the baby at a later stage and/or by somebody else.

To use a breast pump, the breast is typically placed into a funnel-shaped cup and a vacuum is applied such that milk is extracted. A motorized breast pump typically has two operating modes, namely a stimulation mode and an extraction mode. During the stimulation mode, the milk ejection reflex is stimulated. When the breast pump is activated, a pressure source such as a vacuum pump inside the breast pump generates a vacuum and the stimulation mode can be started. The vacuum pump is typically driven by an electric motor. For portable breast pumps, these motors are driven by battery power.

Wearable breast pumps are characterized in that they can be fully worn on the user's body, allowing the user to move around freely. Some of these are small enough to fit into a user's bra. A motor, battery and milk container are for example integrated to form a single unit.

In order to avoid contamination of the pump with milk residue, many breast pumps employ a moveable membrane, known as a diaphragm, between the pump and the expression kit, the membrane forming a barrier against any milk being sucked into the pump. In some breast pumps, the membrane acts furthermore as a massaging element on the nipple, areola and/or breast of the user. The membrane touches parts of the user's breast during the use of the breast pump. There is movement away from the breast when vacuum is applied and towards the breast when vacuum is released. This stimulates the milk release of the user.

An opening in the chamber between the breast and the membrane guides the milk to a collection container. To prevent milk from flowing back into the chamber, it is known to position a valve between the chamber and the container. The valve furthermore separates the pressure changes in the chamber from the volume of the container.

Current breast pumps are often uncomfortable to use, and they do not faithfully replicate breast feeding. They are also made of many parts which have to be dismantled for cleaning. US 2018/154055 discloses a breast shield assembly with a diaphragm. The cavity formed by the breast shield assembly slopes downwardly.

There remains a need for a breast pump system that provides a natural feeling and comfortable action when in use and which has a simple design.

SUMMARY OF THE INVENTION

The invention is defined by the claims.

According to examples in accordance with the invention, there is provided an expression assembly for a breast pump comprising:

- a diaphragm;
- a cover over the diaphragm to define a sealed space between them; and
- a breast shield to which the diaphragm is coupled,
- wherein the diaphragm is formed of a flexible membrane and comprises a cavity having an open end for receiving a nipple of a user and a closed end, wherein the open end has a top and bottom parts connect to the breast shield, wherein:
- the top part is set further back from the closed end in a direction parallel to a central outward axis of the diaphragm than the bottom part; or
- the bottom part is set further back from the closed end in a direction parallel to a central outward axis of the diaphragm than the top part.

This central axis is for example a horizontal axis when the expression assembly is in a default operating orientation.

This expression assembly relates to the parts of a breast pump which deliver milk to a container. In one example, the diaphragm is angled back towards the user at the top. By terminating the top of the diaphragm further back (i.e. closer to the user) than the bottom, the breast is stimulated by contact with the diaphragm further back at the top than at the bottom. This enables the upper jaw movement of a baby during sucking to be simulated and it also enables more stimulation surface to be present.

A milk flow passage is for example defined at the bottom part of the open end, for example between the bottom part of the open end and the breast shield. By having the milk flow passage defined at the back of the bottom of the diaphragm, and set further forward, the milk flow path to the outlet is shorter and the risk of leakage is reduced.

In another example, the diaphragm is angled back towards the user at the bottom. The milk flow passage may be defined at the top part of the open end so that the milk only flow out from the cavity when it has been completely filled.

The design also enables the diaphragm to be assembled with the breast shield in different ways than would otherwise be possible, and thus allows more design freedom. Typically, the diaphragm needs to be pushed along a horizontal axis towards the opening in the breast shield to create an airtight seal. The angled approach enables the diaphragm to be fixed to the breast shield also by a movement that is not horizontal, for example at or near a vertical angle, still creating mounting forces that allow for an airtight seal.

The milk flow passage allows milk to flow out at the bottom of the system. The milk flow passage may for example extend below the level of the opening in the breast shield over which the diaphragm (and cover) are mounted, so that the outward facing part of the breast shield, around the opening to the breast shield, can act as a barrier wall to prevent back flow.

The top part is for example set back by at least 10 mm further than the bottom part.

The diaphragm may further comprise a connecting portion which connects to the breast shield in a plane which, in a normal operating orientation of the expression assembly, is at an angle of between 10 and 20 degrees to the vertical. This is the tilt angle resulting from the way the top of the diaphragm is set back compared to the bottom.

The diaphragm may further comprise a valve closure element for forming part of a valve, the valve closure element extending from a bottom edge of the connection portion (i.e. the bottom of the open end). It is known to provide a valve between the chamber around the nipple and the collection vessel. By integrating a valve closure element of a valve into the flexible membrane, there are few parts and those few parts can be made simple to manufacture, and easy to assemble and disassemble for cleaning.

The breast shield may further comprise a seal for sealing between the rim and the opening of the milk container.

The breast shield may comprise a valve seat for supporting the valve closure element of the diaphragm to form the valve.

The valve closure element is for example for controlling a flow path to a milk container through a first part of a container opening and the diaphragm further comprises a lid for sealing a second part of the container opening.

This diaphragm design incorporates a lid for closing a passage to an open top of a milk container. The diaphragm thus implements the normal diaphragm function of creating a sealed volume to which the vacuum pressure can be applied, but it also forms a valve function and a function of closing the container opening. In this way, the risk of spillage from the container into the rest of the system is reduced, for example as may happen when the user is mobile. The integration of these functions by the single flexible membrane means the assembly can be easily disassembled, cleaned and re-assembled while fitting inside a small, wearable form factor, at a low cost level.

The breast shield for example defines a rim for engaging with the container opening, with a rim opening formed internally of the rim, wherein the valve closure element is for passing through the rim opening during fitting of the diaphragm to the breast shield and the lid is for closing the rim opening after fitting of the diaphragm to the breast shield.

Thus, the fitting of the diaphragm to the breast shield is made simple by having a large rim opening (leading to the container opening) but this is closed once the diaphragm is in place.

The diaphragm may further comprise a positioning tab, the positioning tab extending from a top edge of the connection portion (i.e. at the top of the open end).

The diaphragm may be fitted to a breast shield using this tab, and then hinged down into place. This creates a simple assembly process.

The lid may also comprise a gripping element for fixing the lid to the second part of the rim opening. Thus, the diaphragm is held in place so that the valve function is reliably defined.

The cavity may comprise a ridge which extends from a base of the cavity towards the center of the cavity.

The cavity formed by the flexible membrane thus has an internal ridge (or rim or projection) extending up from a base of the cavity. Thus, the cavity is no longer rotationally symmetric such as a typical conical cavity. The ridge simulates the tongue of a baby, and in use it presses against a lower side of the nipple, simulating the sucking action of a baby. However, it is positioned further forward (away from the breast of the user) than the contact of the top of the diaphragm. This improves user comfort of the breast pump in that it more accurately replicates breast feeding.

The diaphragm for example comprises a first side flow path to a first lateral side of the ridge and a second side flow path to an opposite second lateral side of the ridge. These flow paths facilitate the flow of milk from the closed (back) end of the diaphragm (to which the milk flow is directed) to the open (front) end and then to a container. The use of channels generally is known, but in existing designs the orientation of the rotationally symmetric diaphragm is not fixed, so that such channels are more or less effective in fulfilling this function, depending on their arbitrary rotational position.

The diaphragm may have a fixed rotational orientation (to ensure the ride for tongue simulation is at the bottom) so the flow paths can be designed to be more effective, based on their known orientation.

Another benefit of having a particular positional orientation is that the geometry can be created in such a way that it is more compact around the nipple. The milk flow paths may for example be positioned further away from the central axis, whilst the width of the chamber around the nipple can be kept minimal. This enables a more optimal use of space and thus enables a more compact wearable device. The diaphragm shape can be designed to touch and stimulate the nipple of the user in a predetermined way.

The ridge for example has a flat top to simulate the tongue surface of a baby.

The ridge for example extends from the near the open end to the closed end. Thus, it extends the full depth of the cavity. It may start immediately at the open end, but with a curved transition towards the top of the ridge.

The diaphragm may further comprise a second ridge which extends from the first side of the cavity towards the center of the cavity, and a third ridge which extends from a second side of the cavity towards the center of the cavity. The second and third ridges may for example simulate the lips of the baby by providing additional contact points to the nipple (or other parts of the breast) in addition to the contact of the first ridge which simulates the tongue.

The use of three ridges reduces the volume of the chamber formed between the diaphragm and the breast. The second and third ridges may also extend from near the open end to the closed end.

There may be more than three ridges or there may be only two ridges.

The shape formed by the path around an open end of the cavity is preferably non-rotationally symmetric, for example having a base having a greater radius of curvature than a top. Thus, there is a relatively flat bottom and more rounded to the shape of the open end and hence the shape of the connecting portion.

The shape may better match a typical shape of a baby's mouth. The diaphragm is for example left-right symmetric.

The flexible membrane may have a non-uniform thickness with locally thinner regions to define hinge points. Diaphragm membranes are typically designed with uniform wall thicknesses. By having locally thinner regions, the hinge points can be used to influence the distortion of the flexible membrane to create a peristaltic pumping action such as is created by a baby's mouth.

The flexible membrane for example has a hinge point at the back of the ridge, near the closed end. This hinge point means the ridge can simulate the up and down motion of the tongue.

The invention also provides a breast pump, comprising:

the expression assembly defined above;

a pressure source for delivering an under pressure to the sealed space; and a milk collection container.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 4 shows one example of a design of the diaphragm;

FIG. 9 shows that the cover may have internal ribs;

DETAILED DESCRIPTION OF THE EMBODIMENTS

Figures 1, 2:
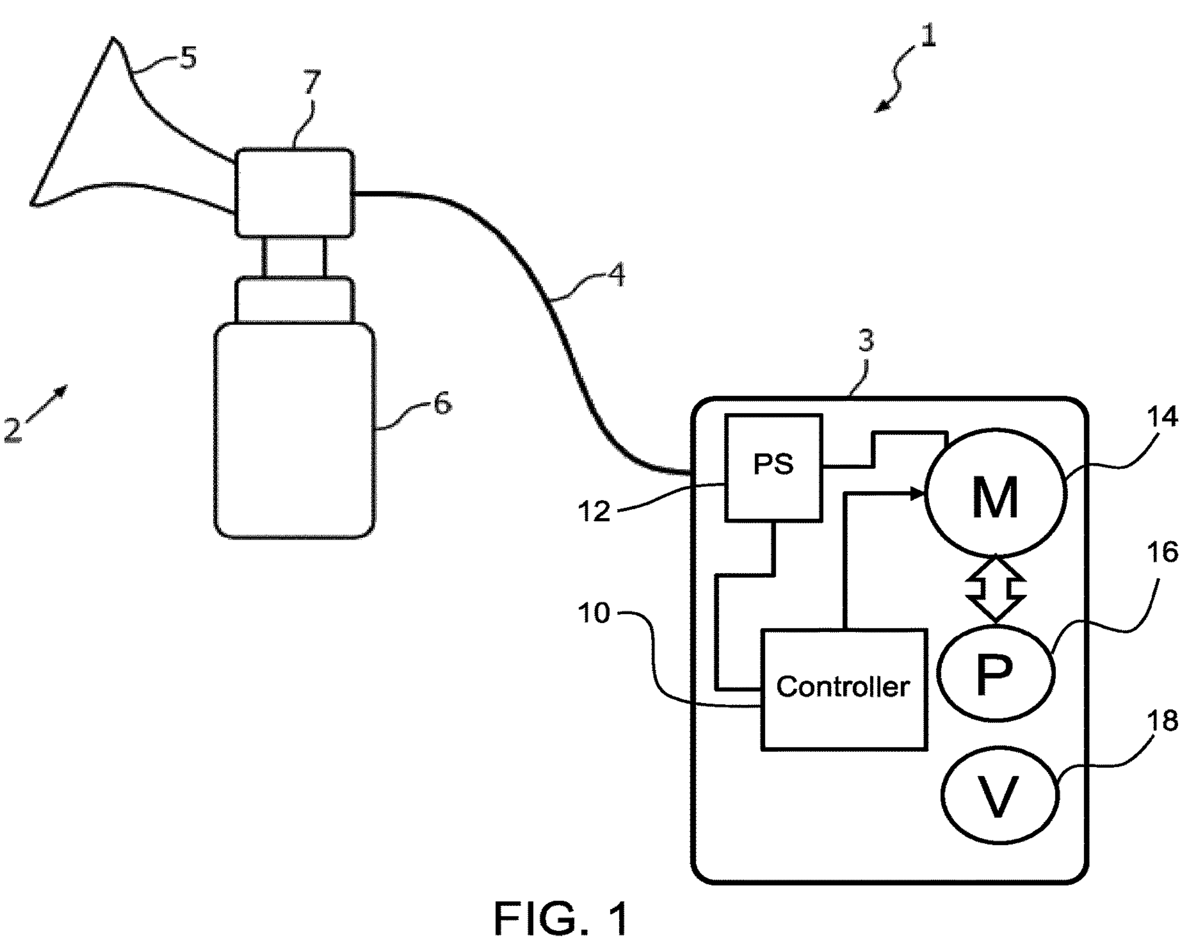
FIG. 1 shows a known breast pump system.
FIG. 2 shows a wearable breast pump.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an expression assembly for breast pump comprising a diaphragm, a cover over the diaphragm to define a sealed space between them, and a breast shield to which the cover and diaphragm are coupled. The diaphragm defines a cavity having an open end for receiving a nipple of a user and a closed end. The open end is angled back at the top to cover more of the top of the breast. This enables the diaphragm to provide better stimulation of the breast as well reducing leakage.

FIG. 1 shows a known breast pump system 1, comprising an expression unit 2 and a drive arrangement for controlling the expression function of the breast pump.

In the example shown, the drive arrangement comprises a pump arrangement 3 which is connected via a tube 4 to the expression unit 2. The pump arrangement includes various components in addition to a pump impeller and the pump motor, so may be considered to be a general operating unit.

The expression unit 2 is formed with a main body 7, a funnel 5 (known as a breast shield) for receiving a breast of a user and a receptacle 6 for collecting the expressed milk. The funnel 5 and the receptacle 6 are connected to the main body 7. The main body 7 comprises a vacuum chamber. A flexible membrane known as the diaphragm is located in the vacuum chamber. The diaphragm prevents expressed milk from flowing into the tube 4 leading to the pump arrangement unit 3.

The operating unit, including the pump arrangement 3, may instead be directly mounted and connected to the main body 7. In this case, the membrane prevents expressed milk from flowing directly into the pump arrangement 3.

The pump arrangement 3 comprises a controller 10, a power source 12, a motor 14 and a vacuum pump 16 (i.e. the impeller driven by the motor 14). The controller controls 10 the operation of the power source 12, motor 14 and vacuum pump 16. The pump arrangement 3 further comprises a solenoid valve 18.

In use, the vacuum pump 16 applies a vacuum to the membrane located in the main body 7 so that it deforms. The membrane deforms to create a vacuum in the funnel 5 which in turns applies a vacuum to the breast which enables milk to be expressed.

The vacuum is applied to the breast at intervals. That is, a pressure differential is applied on a cyclic basis. After a vacuum has been established, the pressure from the vacuum is released by the use of the solenoid valve which is temporarily opened. The solenoid valve is an electromechanically operated valve configured to open and close an air passage that connects to the vacuum side of the vacuum pump to ambient air such that when the solenoid valve is closed, the vacuum pump generates a vacuum in the expression unit which enables milk to be expressed from the breast of a user. When the solenoid valve is opened, the vacuum generated by the vacuum pump is released as ambient air flows towards the vacuum or negative pressure created by the vacuum pump such that the pressure exerted on the breast of a user is partially or completely reduced.

This is a basic description of the known operation of a standard breast pump system.

There are also wearable breast pumps, which are for example for mounting within a feeding bra. All of the drivetrain components described above are then formed within an outer enclosure which fits over the breast. A top part contains the drivetrain (pump, motor, controller) and a bottom part forms the collection vessel. This enables breast pumping to be performed more discretely.

There are also other types of wearable breast pump whereby the expression unit is fixed to a breast and the pump unit and/or milk container are situated elsewhere on the body of a user.

FIG. 2 shows a wearable breast pump, comprising an expression kit 30 attached to a respective milk collection vessel 31.

This invention in some aspects relates to the design of the flexible membrane, and particularly for a wearable breast pump design such as shown in FIG. 2. In other aspects, the invention relates to the assembly and disassembly of different parts of a wearable system.

Figure 3:
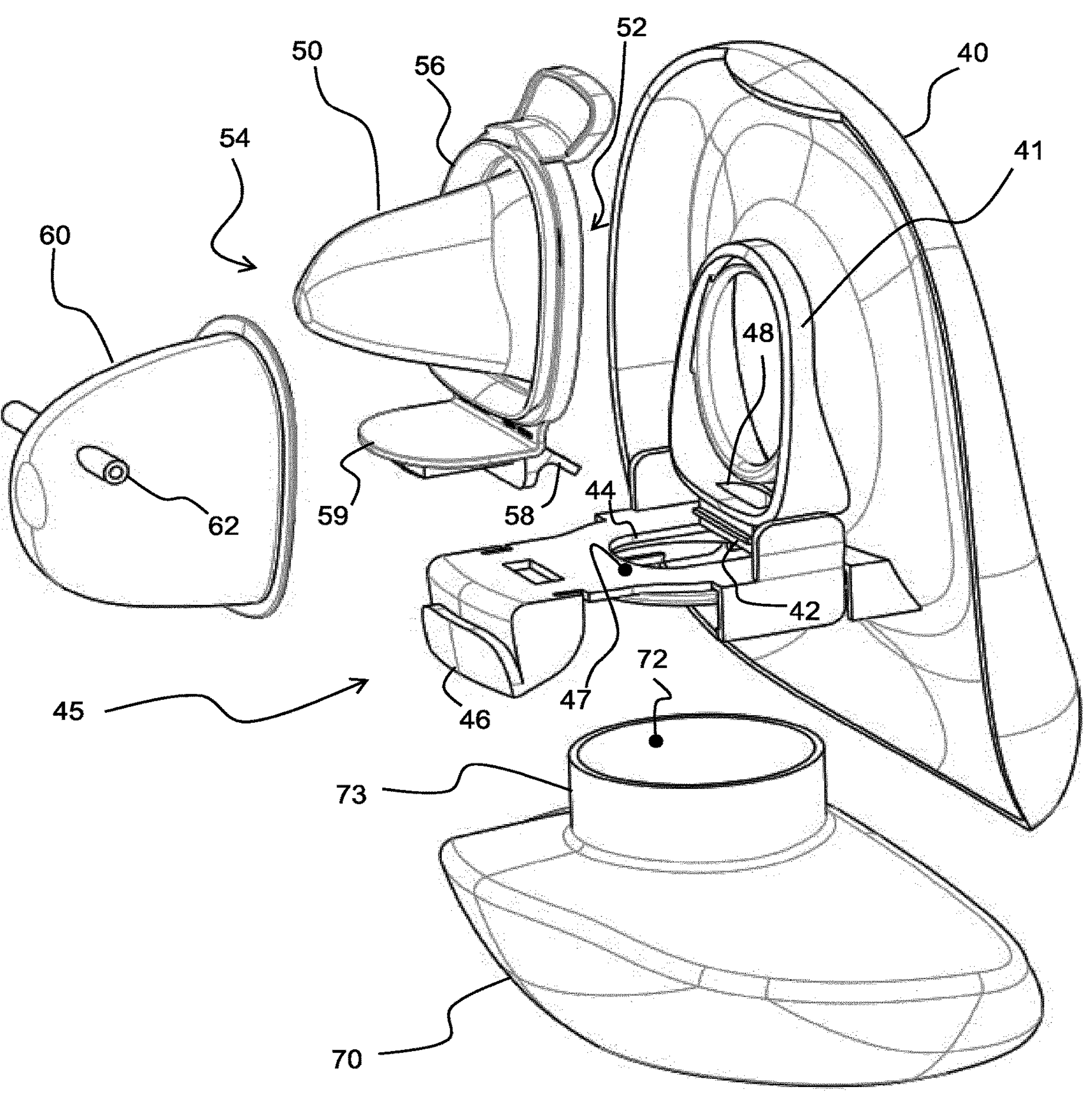
FIG. 3 shows a breast shield, a diaphragm and a cover over the diaphragm to define a sealed space between them and a milk collection container.

FIG. 3 shows the parts of one example of a design in accordance with the invention. The parts shown relate to the milk flow. FIG. 3 thus shows some internal parts of a breast pump, but does not show an outer housing or the vacuum source or associated control circuitry (i.e. controller, battery, valves etc.).

FIG. 3 shows a breast shield 40, a diaphragm 50 formed as a flexible membrane and a vacuum cover 60 over the diaphragm 50 to define a sealed space between them. A milk collection container 70 is also shown. The cover 60 has a port 62 for coupling pressure from the vacuum source (not shown) to the sealed space between the diaphragm 50 and the cover 60.

The diaphragm 50 defines a cavity having an open end 52 for receiving (at least) a nipple of a user and a closed end 54. A connecting portion 56 in this example extends around the open end 52. It is for fitting over an opening of the breast shield 40 defined by a connection collar 41. A part of the connecting portion facing the user is for connecting the diaphragm to the collar 41 of the breast shield 40 and a part of the connecting portion 56 facing away from the user is for connecting the diaphragm to the cover 60. There is thus a connection portion 56 for connecting the diaphragm to the breast shield and/or the vacuum cover 60.

The breast shield includes an integral frame to which the other parts of the breast pump may be connected. The frame includes a release element 45 which projects forwards (i.e. away from the user) from the main body of the breast shield. As explained further below, the breast shield 40 and the diaphragm form a rear assembly for fitting over the breast of a user. A front assembly fits over the rear assembly and includes the cover 60, the electrical parts of the breast pump, namely the power source (battery), pump and controller, as well as a front cover. The front assembly thus fits to, and forms a connection with, the frame, and the frame also supports the milk container. Thus, the front assembly can be removed leaving the milk container attached to the frame.

The release element 45 extends partly or fully through a channel in the front assembly, thereby to define a release actuator 46 at the front of the breast pump. In other designs, the release actuator may be at a side.

The breast shield 40 and release element 45 are formed as a single integral item.

Along the frame of the breast shield there is a rim 47 for engaging with an opening 71 of the milk container 70 formed by a top neck part 73. A rim opening 44 is formed internally of the rim 47. The milk container 70 can thus be docked reliably to the rim 47 as this a rigid part of the breast shield. Thus, the breast shield, and in particular the release element 45, acts as the support for the milk container as well as providing the support for the front assembly. A seal may be provided for sealing between the underside of the rim 47 and the opening 72 of the milk container.

The rim opening 44 has a front part (seen in FIG. 3) and a rear part. The rear part of the rim opening has a top channel 48 which leads to a valve seat 42. The top channel 48 is the milk flow passage from the cavity formed by the diaphragm to the milk container 70.

The opening defined by the collar 41 of the breast shield is smaller than the opening of the open end 52 of the cavity of the diaphragm (at least at a lower area) such that milk is always caught against the outside of the opening to the breast shield and led to the container 70.

When a vacuum is applied to the sealed space between the diaphragm 50 and the cover 60 (i.e. the opposite side of the diaphragm to the cavity), the diaphragm expands compared to a rest-state when vacuum is not applied. The membrane of the diaphragm 50 touches at least one part of the breast, typically the nipple but possibly the areola and/or the breast. In the rest state, the diaphragm is non-rotationally symmetric.

Milk is expressed into the cavity in use, and is ejected towards the closed end 54 (the back) of the cavity from where it then flows to the open end and into the collection container 70.

The breast shield 40 is made of a different material to the flexible membrane of the diaphragm 50, e.g. polypropylene for the breast shield and silicone for the flexible membrane of the diaphragm. This is for ease of cleaning, for ease of use and for manufacturing reasons.

The diaphragm has a valve closure element 58, formed as in integral part of the flexible membrane, for forming part of a valve. The valve closure element may be a valve closure element of any type of valve. The valve closure element 58 is for example a flap of a flap valve. This flap valve is in the flow path from the cavity to the milk container 70 via the top channel 48.

The flap 58 extends from a bottom edge of the open end 52 of the cavity. The valve seat 42 formed by the breast shield defines the seating location for the flap valve. By integrating the movable part of a valve, in this example the flap of a flap valve, into the flexible membrane of the diaphragm, there are few parts and those few parts can be made simple to manufacture, and easy to assemble and disassemble for cleaning.

The valve may instead be formed entirely by the diaphragm.

The diaphragm also defines a lid 59. The lid 59 is for sealing the front (second) part of the rim opening 44. The purpose of the rim opening is to make the diaphragm easy to position and couple to the breast shield, while reliably placing the valve closure element in its required position. In particular, the flap 58 is fed through the front part of the opening 44 into a position where it rests (upwardly) against the valve seat 42. Thus, the flap passes through the rim opening 44 during fitting of the diaphragm to the breast shield and the lid 59 closes the rim opening 44 after fitting of the diaphragm to the breast shield. As shown more clearly below, the valve seat faces downwardly and the valve flap is biased upwardly against the valve seat.

Once in position, the lid 59 closes the front part of the opening 44 so that the only entrance to the container is via the top channel 48 and the valve. The milk collection container has a single opening 72 but it may be considered to define first and second parts; a first part beneath the valve seat 42 and a second part beneath the second part of the rim opening 44. Thus, the valve closure element provides a flow path to a milk container through a first part of the milk container opening and the lid closes a second part of the milk container opening.

The lid 59 for example comprises a gripping element for fixing the lid to the second part of the rim opening. This is for example a tab or rib or rim which is pushed through the opening 44 and engages the underside of the rim 47.

The container 70 clips to the underside of the rim 47, for example with a snap fit or with a push and rotate (bayonet) coupling.

The diaphragm thus implements the normal diaphragm function (creating a sealed volume to which the vacuum pressure can be applied), a flap valve function and a function of closing the container opening (by closing the rim opening provided to simplify the connection of the diaphragm to the breast shield). In this way, the risk of spillage from the container into the rest of the system is reduced, for example as may happen when the user is mobile. The integration of these functions by the single flexible membrane means the assembly can be easily disassembled, cleaned and re-assembled while fitting inside a small, wearable form factor, at a low cost level.

The diaphragm with its integrated valve is asymmetrical (i.e. not rotationally symmetric about a horizontal axis), so that the breast pump can be assembled only in one specific way or in a set of specific ways (if there is some rotational symmetry, e.g. rotational symmetry of order 3 for a triangular design). This has the advantage that the flexible membrane shape can be formed to touch and stimulate the nipple of the user in a predetermined way.

Furthermore, in the design shown, there are only three elements of the breast pump that come into contact with the breast milk, and need to be cleaned in a regular and thorough way, namely the breast shield 40, the membrane 50 with integrated valve 58 and lid 59 and the milk container 70.

These form the same rear assembly and the container, and may thus be removed from the remainder of the breast pump as a unit. The front assembly may be removed leaving the rear assembly and the connected container, because the container is supported by the breast shield.

FIG. 4 shows one example of a design of the diaphragm 50. The left image shows a perspective view and the right image shows a view looking into the open end 52 of the cavity.

The diaphragm comprises a radially inwardly projecting ridge 80. It extends from a base 82 of the cavity towards the center of the cavity. The ridge is preferably convex shaped so that no milk pooling can take place on the ridge. In general, the shape of the diaphragm is such that milk, in normal use, always flows towards the container.

The cavity formed by the flexible membrane thus has an internal ridge 80 extending up from a base of the cavity. The cavity is no longer rotationally symmetric such as a typical conical cavity. The ridge is a tongue-simulation ridge for simulating the tongue of a baby, and in use it presses against a lower side of the nipple, simulating the sucking action of a baby. This improves user comfort of the breast pump in that it more accurately replicates breast feeding. The ridge projects to a position which represents the position of the surface of the tongue of a baby. It may also be designed to move during application of a controlled pressure to simulate the movement of the tongue during feeding.

A first side flow path 84 is formed to a first side of the ridge 80 and a second side flow path 86 is formed to an opposite second side of the ridge 80. These flow paths facilitate the flow of milk from the closed (back) end of the diaphragm (to which the milk flow is directed) to the open (front) end 52 and then to the container. The fixed rotational orientation of the diaphragm, with the ridge projecting upwardly from the bottom, means the flow paths 84, 86 can be designed to be more effective, based on their known orientation.

The flow paths slope downwardly from the closed end of the cavity to the open end of the cavity.

The diaphragm has a default orientation in which a central axis (pointing outwardly from the user) is horizontal. In this default orientation, the top of the ridge 80 is horizontal and hence parallel with a central outward axis of the cavity. The flow paths for example slope downwardly in the range 20 to 40 degrees relative to the horizontal, i.e. relative to the ridge direction. This means that there is a range of body feeding angles of the mother which still enable the expressed milk to flow freely to the milk collection container 70.

The flow paths at the left and right of the ridge also allow for the user to angle to the left or right without leakage. Their depth at the open end of the cavity, relative to the position of the opening of the breast shield, allows the user to lean backward again without leakage. The slope of the incline mentioned above between the closed end of the cavity and the open end allows the user to lean forward without pooling of milk.

The cavity has a compact design around the nipple. The milk flow channels formed by the flow paths may for example be positioned further away from the central axis without significantly increasing the volume of the cavity, by keeping the width of the chamber around the nipple to smaller dimensions.

The ridge 80 extends most of the depth of the cavity, for example at least 50%, preferably at least 75% of the depth of the cavity (i.e. the distance between the open end and the closed end). It for example extends from the near the open end to the closed end. It may start immediately at the open end, but with a curved transition towards the top of the ridge.

The ridge 80 for example occupies an angle β around the cavity opening 52 in the range 30 to 100 degrees. The ridge for example extends from the outer edge of the open end towards the center of the open end by at least 30%, for example at least 40%, for example by at least 50% of the (vertical) radius of the open end.

FIG. 4 shows second ridge 90 which extends from the first side of cavity towards the center of the cavity above the first flow path 84. There is also third ridge 92 which extends from a second side of the cavity towards the center of the cavity above the second flow path 86. The second and third ridges also extend from near the open end to the closed end. They may result in a rotationally symmetric design (with rotational symmetry of order 3) so that there are three equivalent fixed orientations with which the diaphragm may be fixed.

The second and third ridges may be designed to move when the flexible membrane deforms so that they may simulate movement the lips of the baby by providing additional contact points to the nipple in addition to the contact of the first ridge which simulates the tongue.

However, the second and third ridges may instead not move significantly when the membrane deforms, and they may instead be provided for copying the shape of a baby's lips and/or jaws rather than simulating their movements.

The use of three ridges further reduces the volume of the cavity formed between the diaphragm and the breast.

By additionally limiting the volume of the sealed space between the diaphragm and the cover, a minimum of air is needed in the system on the pump side, thus reducing dead space and increasing the efficiency of the pump system.

The design with three ridges defines a triangular arrangement of ridges. However, there may be only a single bottom ridge, or an upper ridge and a lower ridge, or more than three ridges.

As can be seen in FIG. 4, the shape of the open end of the cavity, i.e. the shape formed by the path around the connecting portion 56, is also non-rotationally symmetric (as well as the internal volume of the cavity being non-rotationally symmetric). For example, it has a flatter base than top, to better match the typical shape of a baby's mouth. The shape of the open end, and indeed the diaphragm as a whole, may be left-right symmetric.

The flexibility of the flexible membrane of the diaphragm enables the contact areas to move so as to accommodate different nipple sizes.

FIG. 4 additionally shows an optional positioning tab 94 extending from a top edge of the open end, i.e. extending upwardly from the connection portion 56. The positioning tab is used to simplify the connection of the diaphragm to the breast shield 40, discussed further below.

Figure 5:
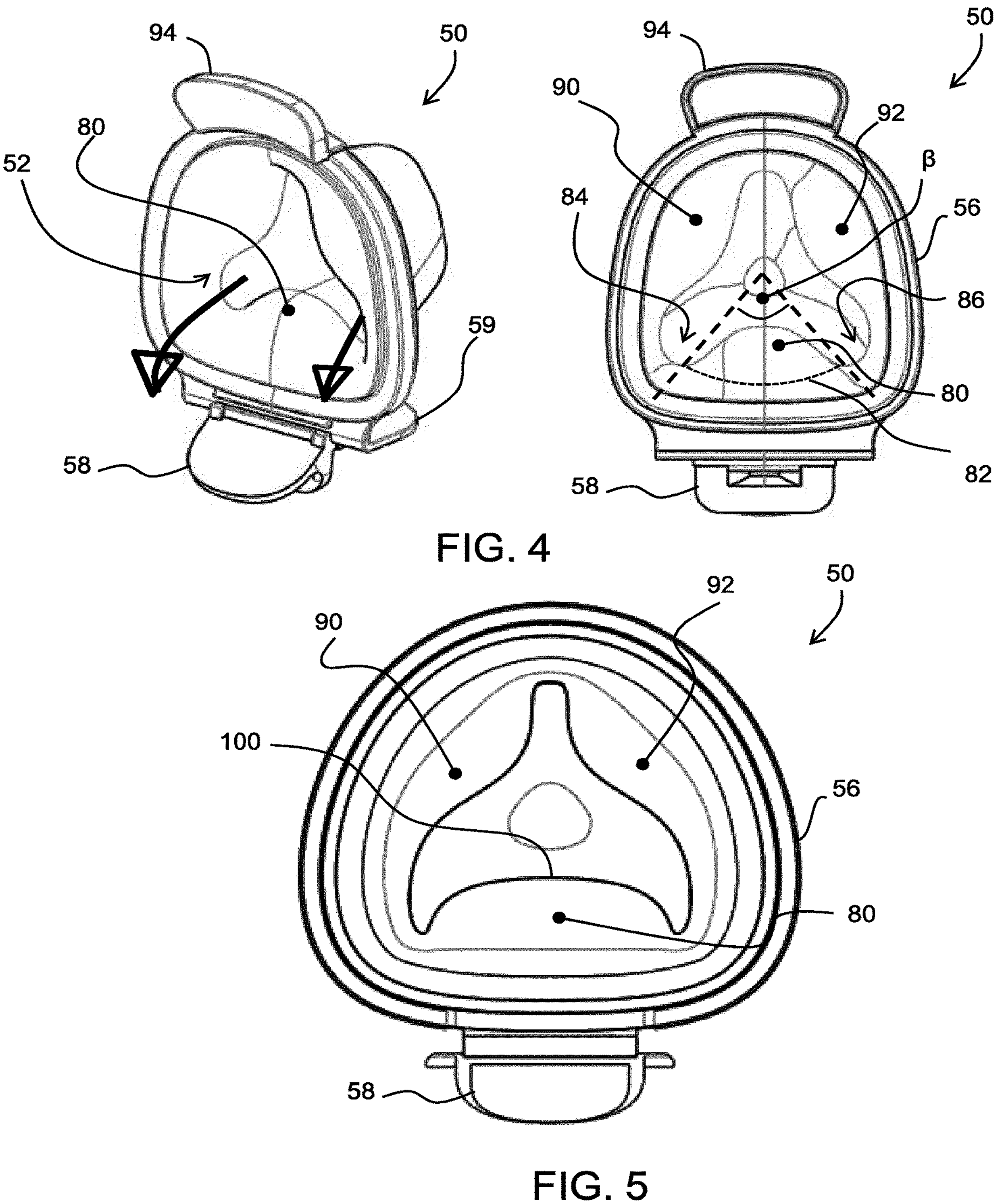
FIG. 5 shows a slightly different design of the diaphragm to FIG. 4.

FIG. 5 shows a slightly different design of the diaphragm, in which the ridge 80 has a flat top 100 to simulate the tongue shape.

Figure 6:
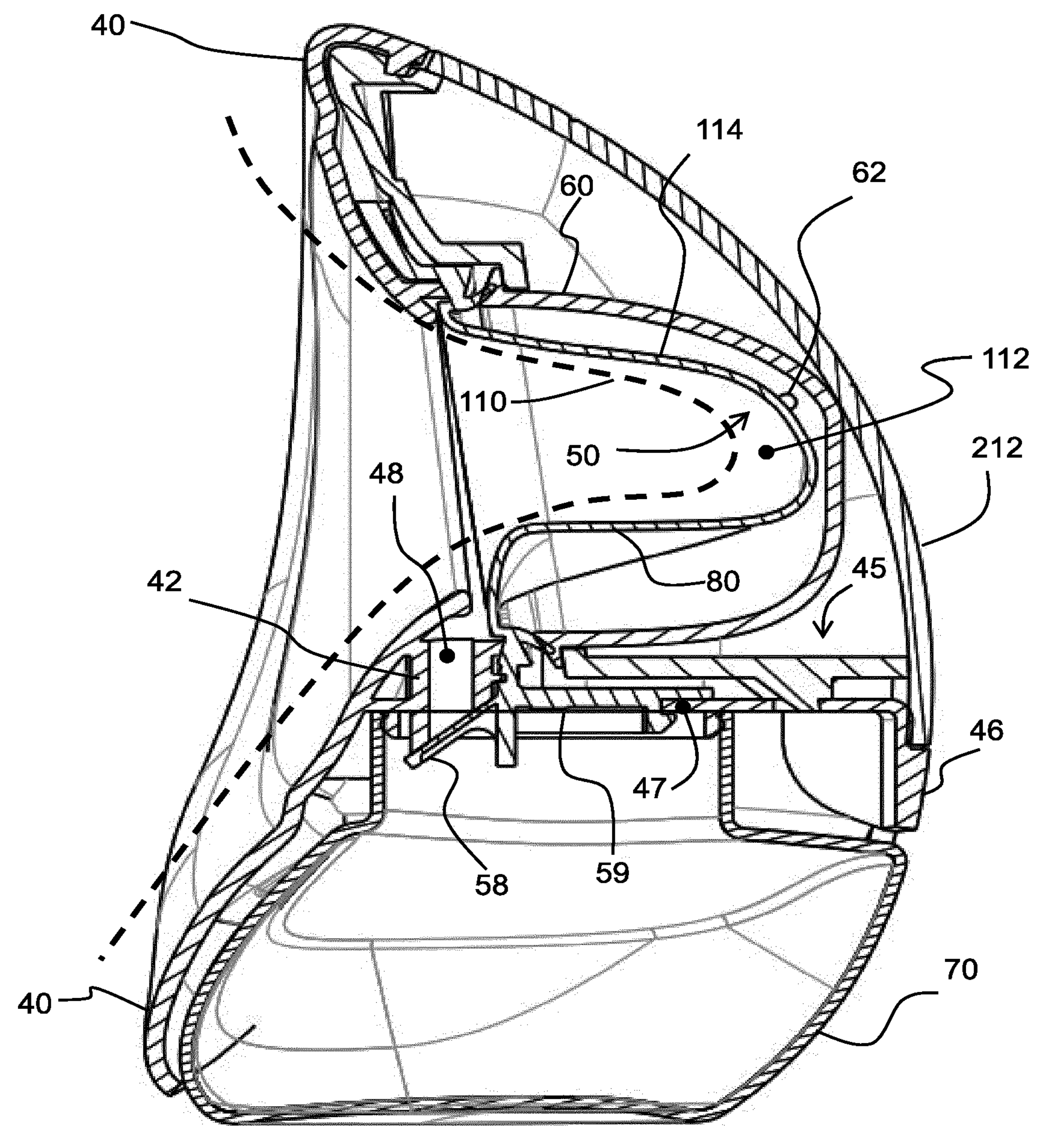
FIG. 6 shows a cross section of the assembled breast pump applied to the breast.

FIG. 6 shows a cross section of the assembled breast pump applied to the breast. The nipple 110 is received by the cavity 112 formed by the flexible membrane 114 of the diaphragm 50.

The ridge 80 is shown as having a horizontal top edge (which may be flat or rounded in front view as shown in FIGS. 4 and 5).

FIG. 6 also shows how the lid 59 engages under the rim 47 to hold the diaphragm in place and also to set the position of the flap 58. The outer cover 212 of the front assembly is also shown.

Figure 7:
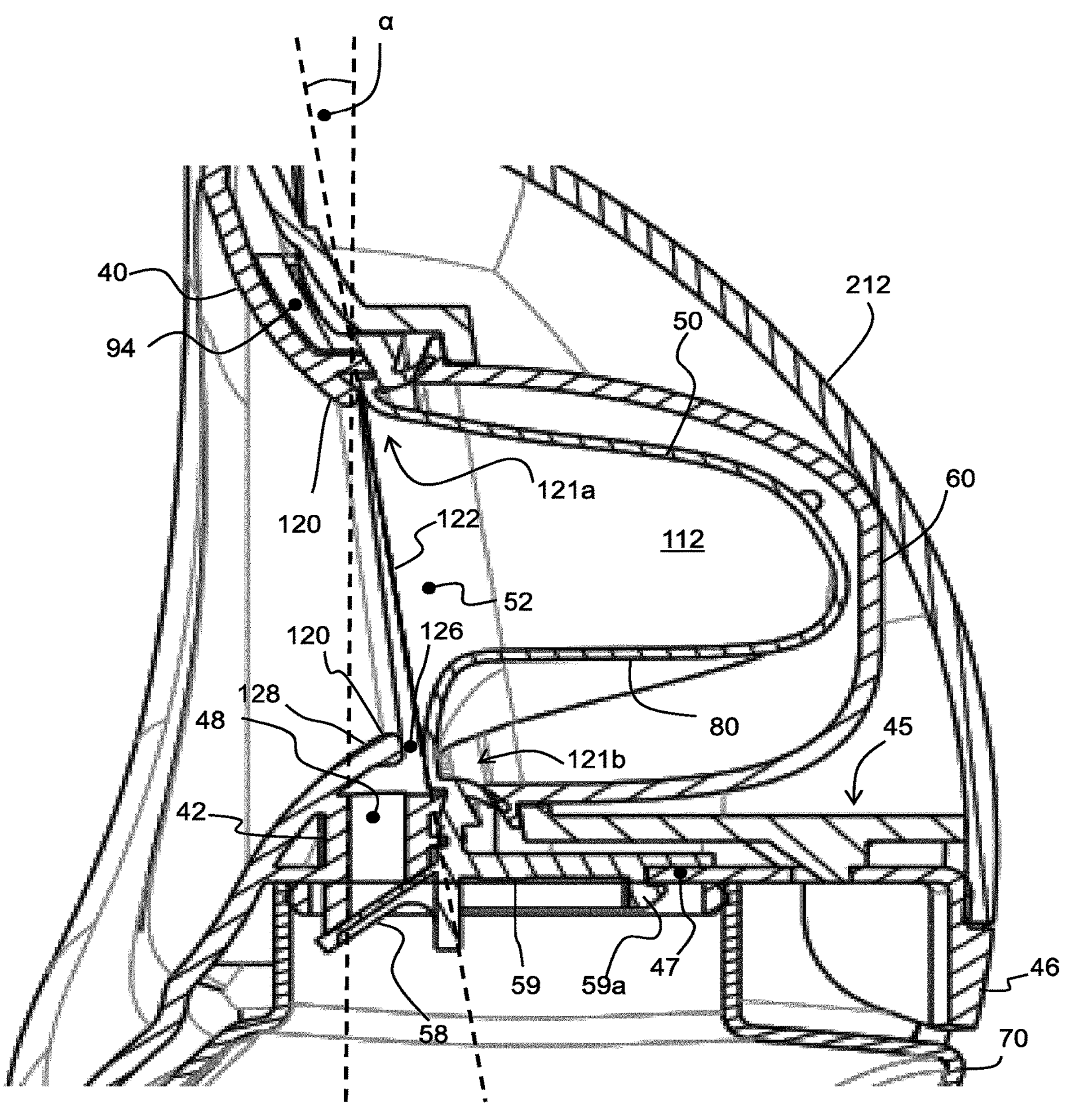
FIG. 7 explains an alignment between an opening of the breast shield and the diaphragm.

FIG. 7 shows a design feature more clearly, as an enlarged image of part of FIG. 6. The design feature relates to the orientation of the components and is to simplify assembly and disassembly and also to improve breast stimulation during milk expression. FIG. 7 shows that the breast shield 40 has an opening 120 over which the cover 60 and diaphragm 50 are coupled.

The open end 52 of the cavity 112 has a top part 121*a* which connects to the breast shield 40 and a bottom part 121*b*, with a milk flow passage 126 defined at the bottom part, in particular as a gap or channel opening between the bottom part 121*b* and the breast shield 40. The top part 121*a* is set further back from the closed end in a direction parallel to a central outward axis of the diaphragm than the bottom part. In other words it is set back further along a horizontal direction (when the breast pump is being worn by a mother in an upright standing pose), i.e. closer to the user. The top part 121*a* is for example set back horizontally (i.e. parallel to the ridge 80) by at least 10 mm further than the bottom part 121*b*. The central outward axis is forward axis (i.e. it is in a normal forward direction faced by the wearer, i.e. horizontal when the wearer is standing upright).

The diaphragm may be considered to be angled back at the top, for example by an angle $\alpha$ as shown in FIG. 7. This angle is for example in the range 10 to 20 degrees. The connecting portion 56 formed at the open end of the cavity for example connects to the breast shield in a plane 122 which is thus (in a normal operating orientation of the expression assembly), is at an angle $\alpha$ of between 10 and 20 degrees to the vertical.

There is a gap 126 between the bottom of the opening 120 and the bottom of the open end 52 and this defines a milk flow passage. This gap leads to the top channel 48.

The opening 120 of the breast shield is smaller than the open end 52, in particular at the bottom so that the opening 120 overlaps the open end. A lip 128 which forms the bottom of the opening 120 thereby blocks milk and ensures all flow reaches the container via the top channel 48. This lip 128 extends partly over the top channel 48 (leading to the valve), to act as a barrier to prevent splash back from the container to the breast pump.

The lip 128 also means that the first and second side flow paths (on opposite sides of the tongue-simulation ridge) are directed against the lip. Thus, the ends of the first and side flow paths at the open end of the cavity are positioned outside the area of the opening 120 in the breast shield (i.e. below the opening 120) so that milk is directed to the outlet.

There is preferably a seal all around the interface between the breast shield 40 and diaphragm 50 except at the bottom where the milk flow passage 126 is formed. Instead of a top channel 48 defined within in the collar, the milk flow passage may be formed as a notch set back into the opening 120 of the breast shield.

By terminating the top of the diaphragm further back (i.e. closer to the user) than the bottom, the breast is stimulated by contact with the diaphragm further back at the top than at the bottom. This enables the upper jaw movement of a baby during sucking to be simulated and it also enables more stimulation surface to be present. By having the milk flow passage defined at the back of the bottom of the diaphragm, and set further forward, the milk flow path to the outlet is shorter and the risk of leakage is reduced.

The angled interface allows for the diaphragm to be assembled with the breast shield in different ways than would otherwise be possible, and thus allows more design freedom.

To assemble the parts, if the optional positioning tab 94 is provided, it is coupled to a receiving area of the breast shield 40. This may be achieved with a significant amount of freedom of movement, and does not need to be a perfectly horizontal fitting. The diaphragm is then pivoted down into position using this positioning tab as a pivot.

The flap of the valve 59 is inserted through the rim opening defined by the rim 47 and brought into engagement with the underside of the valve seat 42. The lid 59 is then fixed to the opening by pushing a retaining tab or tabs 59*a* through the opening. This then seals the rim opening, leaving the top channel 48 as the only fluid path between the cavity and the container.

The cover 60 is then positioned, in particular as a part of an overall front assembly. The cover 60 secures the diaphragm into its end position. The element 130 is another part of the front assembly and it holds the cover 60 in place. The front assembly which includes the cover 60 also has an external front housing of the breast pump.

It can be seen that the assembly involves coupling of positioning tab 94 as a simple coupling, followed by a pivot motion to attach the diaphragm to the breast shield, and finally connection of the cover 60, diaphragm 50 and breast shield 40 using a front assembly. The tab 94 is optional, and the diaphragm may simply be slid over the connection collar 41 of the breast shield and then fixed in place using the lid 59.

The examples above show a uniform wall thickness of the flexible membrane which forms the diaphragm.

Figure 8:
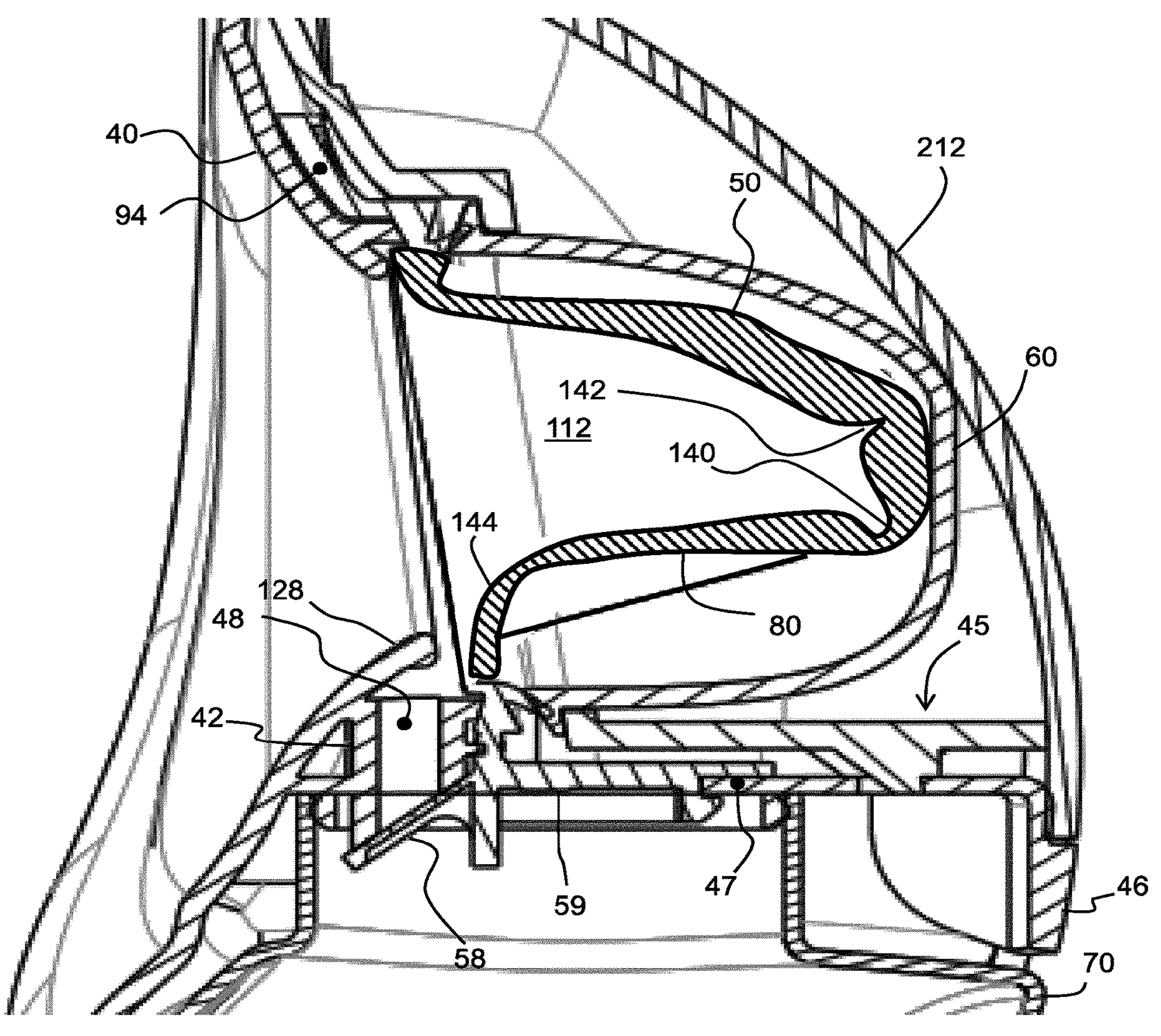
FIG. 8 shows a design of the diaphragm in which the flexible membrane has a varying thickness.

As shown in FIG. 8, the flexible membrane of the diaphragm may have a varying thickness.

For example, the part of the membrane which defines the cavity 112 may have a smaller thickness near the open end than near the closed end. This may be used to effect peristaltic actions when vacuum is applied. In particular, the cavity may move in an axial direction due the greater elasticity at the open end, compared to lower elasticity of the remainder of the cavity wall.

To control the deformation characteristics, the flexible membrane may be locally strengthened by ribs or protrusions. In addition, FIG. 8 shows locally thinner regions 140,142 to define hinge points. By having locally thinner regions, the resulting hinge points can also influence the distortion of the flexible membrane to create a desired peristaltic pumping action such as is created by a baby's mouth.

The flexible membrane for example has a hinge point 140 at the back of the ridge 80, near the closed end. This hinge point helps to create an up and down motion of the tongue as well as the in and out movement formed by the thinner region 144 at the open end of the cavity.

The use of strengthening ribs also may be used to enable the movement of the flexible membrane to be restricted to avoid the creation of an undesirably large amount of under pressure on the breast side.

As mentioned above, by limiting the volume of the sealed space between the diaphragm and the cover, a minimum of air is needed in the system on the pump side, thus reducing dead space and increasing the efficiency of the pump system.

FIG. 9 shows that the cover 60 may have internal ribs 150. Two different rib designs are shown. These may be used both to reduce the dead volume of the pump but also to influence the deformation characteristics of the flexible membrane of the diaphragm. For the same purpose, the diaphragm may have external ribs.

It is mentioned above that the breast pump comprises three modules.

Figures 10, 11, 12:
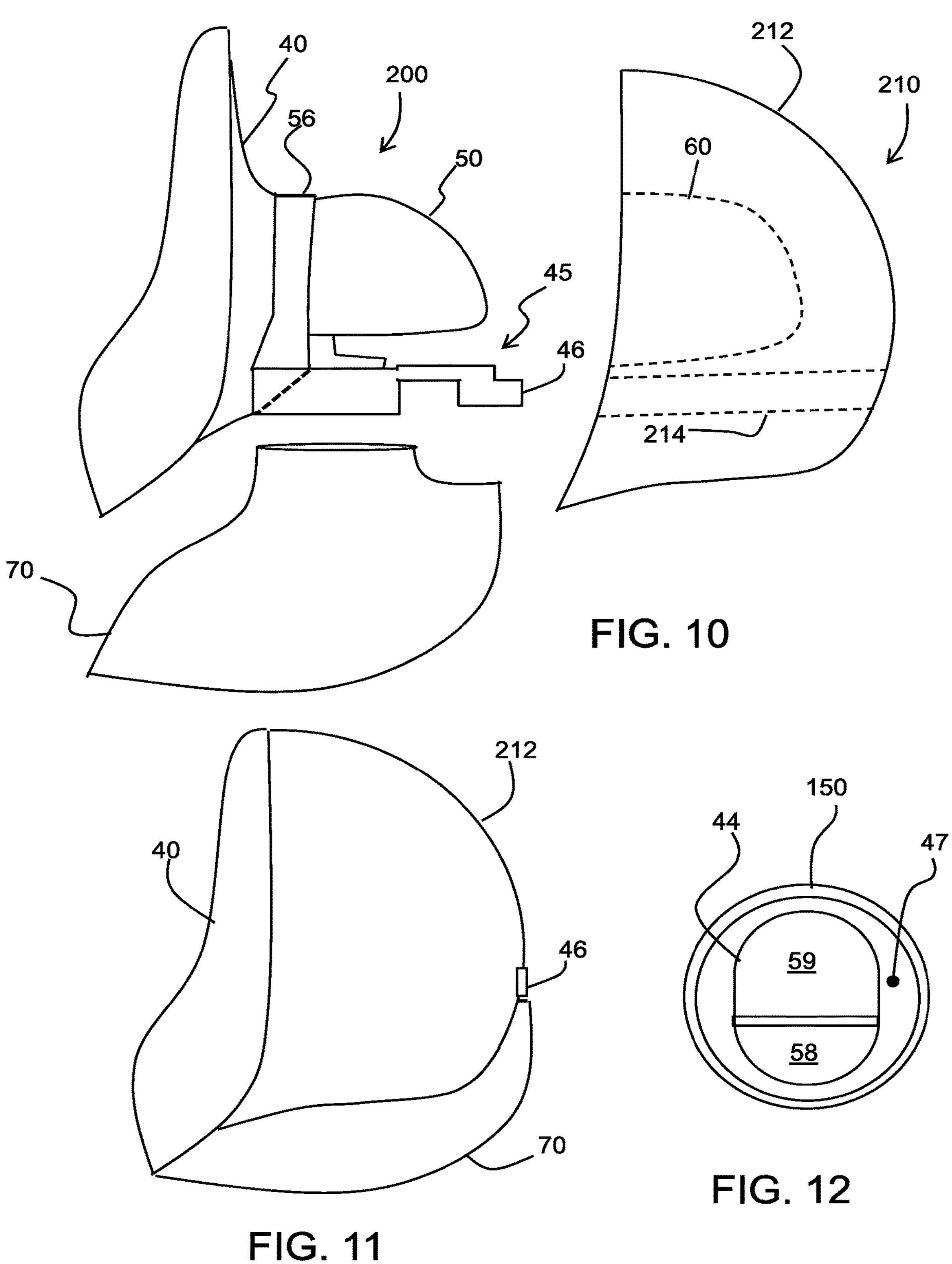
FIG. 10 shows in exploded view that the breast pump comprises three modular parts.
FIG. 11 shows the three modular parts coupled together.
FIG. 12 shows the rim by which the breast shield engages with the milk container.

FIG. 10 shows the three modules in exploded view.

A first module is a rear assembly 200 is for fitting over the breast of a user. It comprises the breast shield 40 (and integrated release element 45) and the diaphragm 50. A second module is a front assembly 210 for fitting over the rear assembly. It comprises the cover 60 for fitting over the diaphragm 50 to define a sealed space between them, a power source, pump and controller (and valves etc.) and a front cover 212.

The release element 45 projects forwards through a channel 214 in the front assembly to define a release actuator at a front of the front assembly. It could be exposed at the front surface or it could lie just beneath the surface, for example as a push button beneath a flexible cover.

The third module is the milk container 70, which fits beneath the rear and front assemblies.

This breast pump design is easy to assemble and disassemble for the user, by forming a rear assembly from a breast shield and a diaphragm. These are the parts (other than the container) which may come into contact with milk and therefore require regular and thorough cleaning. By forming them as an assembly, and providing the remaining parts (pump, outer housing etc.) as a front assembly, the assembly and disassembly is made simple.

The breast shield acts as support for the remaining parts of the breast pump. The breast pump can be disassembled from the front side by actuating the release actuator 46.

FIG. 11 shows the three modular parts coupled together.

FIG. 12 shows the rim 47 by which the breast shield engages with the top opening of the milk container 70. The rim opening 44 has a first part which is closed by the lid 59 and which leads to a first area of the opening to the milk container, and a second part which at which (or through which) the valve seat is provided and is closed by the flap 58.

Figure 13:
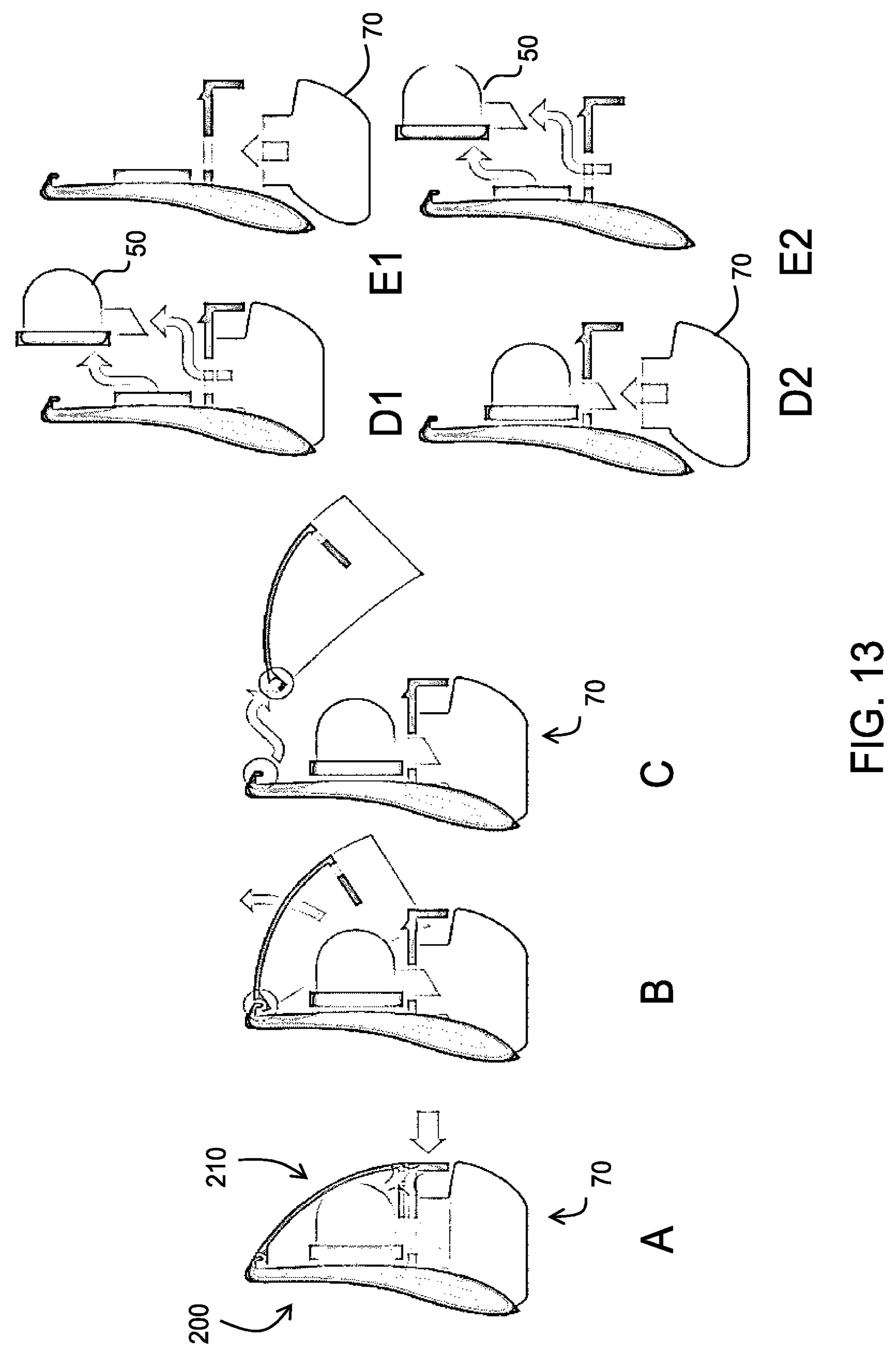
FIG. 13 shows two possible disassembly routines.

FIG. 13 shows two possible disassembly routines.

In step A, the breast pump is assembled. The release actuator 46 is operated to unlatch the front and rear assemblies.

In step B, the front assembly is pivoted up. The front and rear assemblies have a releasable hinge connection at the top for this purpose.

Once opened up, the hinge connection can be released as shown in step C so that the front assembly is removed. The milk container remains attached to the breast shield of the rear assembly.

In step D1, the diaphragm 50 is removed and then in step E1 the milk container is removed.

Alternatively, in step D2, the milk container is removed and then in step E2 the diaphragm is removed.

Figure 14:
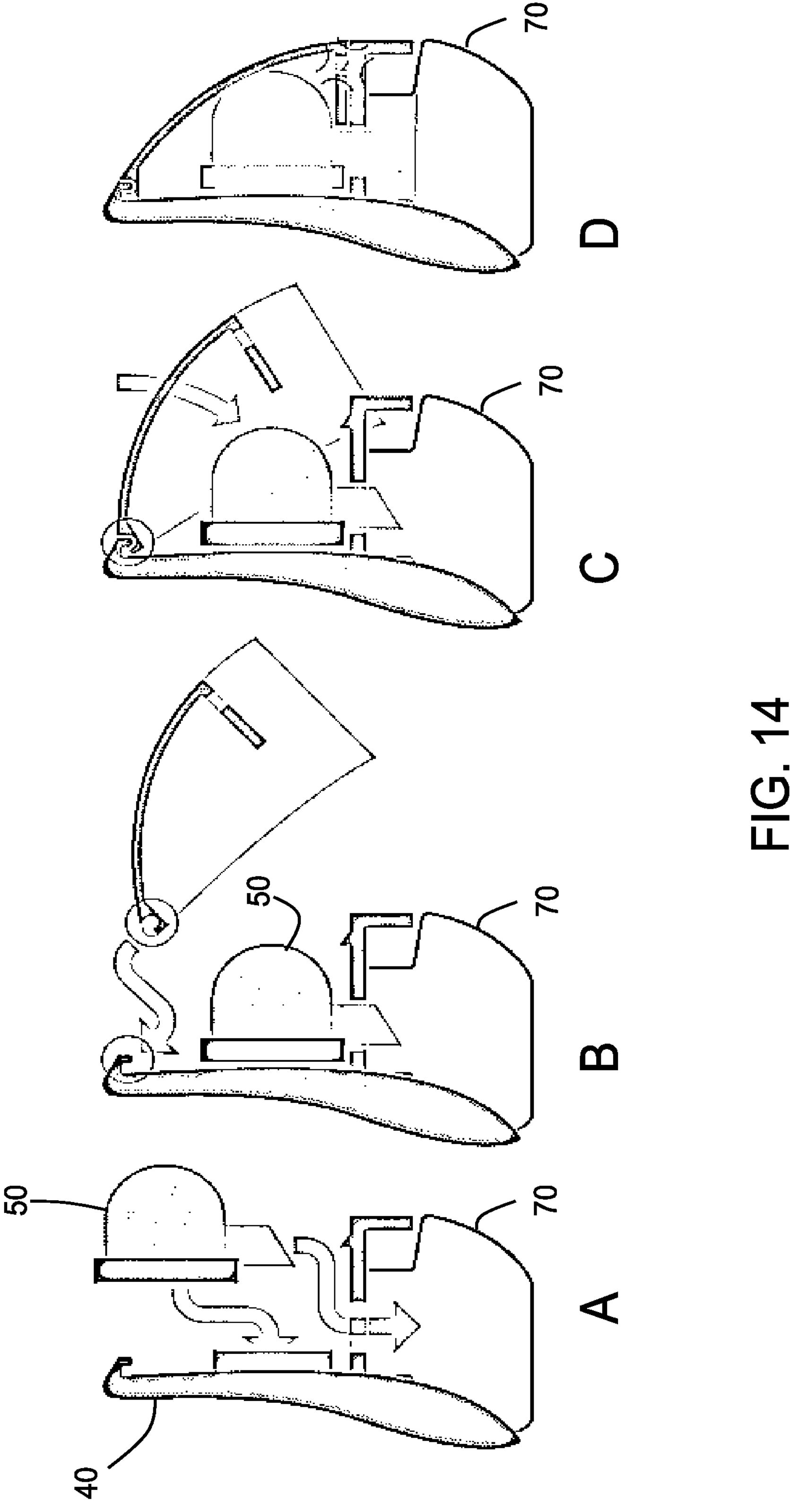
FIG. 14 shows an assembly routine.

FIG. 14 shows an assembly routine.

In step A the container 70 is fitted and the diaphragm 50 is fitted to the breast shield 40 (in either order) to create the complete rear assembly with container attached.

In step B the front assembly is engaged with the rear assembly at the top hinge.

In step C the front assembly is pivoted closed over the rear assembly.

In step D the front assembly clicks into engagement with the rear assembly.

The rear assembly and the front assembly may for example engage by a snap fit and the release actuator 46 releases the snap fit coupling.

The snap fit coupling may be provided on the release element 45 or on the rear assembly. Similarly, the milk collection container could be locked into place using snap fit elements or a twist and lock coupling to the rim 47.

The breast facing side of the breast shield may have a soft a cushion to improve comfort.

The coupling of the front assembly may instead use hooks to first provide an anchor to the breast shield, followed by a rotary motion lock the assemblies into place. Alternatively, the coupling may use linear sliding motion to first position elements in a guiding track, and then lock them into place.

The release element 45 may be hidden within the outer contour of the assembled breast pump system, or it can be fully or partially exposed on the outside, opposite the breast of the user when in use. As the flexible release button is integrated as part of the breast shield, the front assembly can easily be manufactured in a well-sealed and self-contained manner, for example protecting the electrics and electronics from liquids. Two-shot molding or similar techniques may be used to add materials with different characteristics, for example for release element, for sealing to the milk container or for providing a soft interface to the user.

Figure 15:
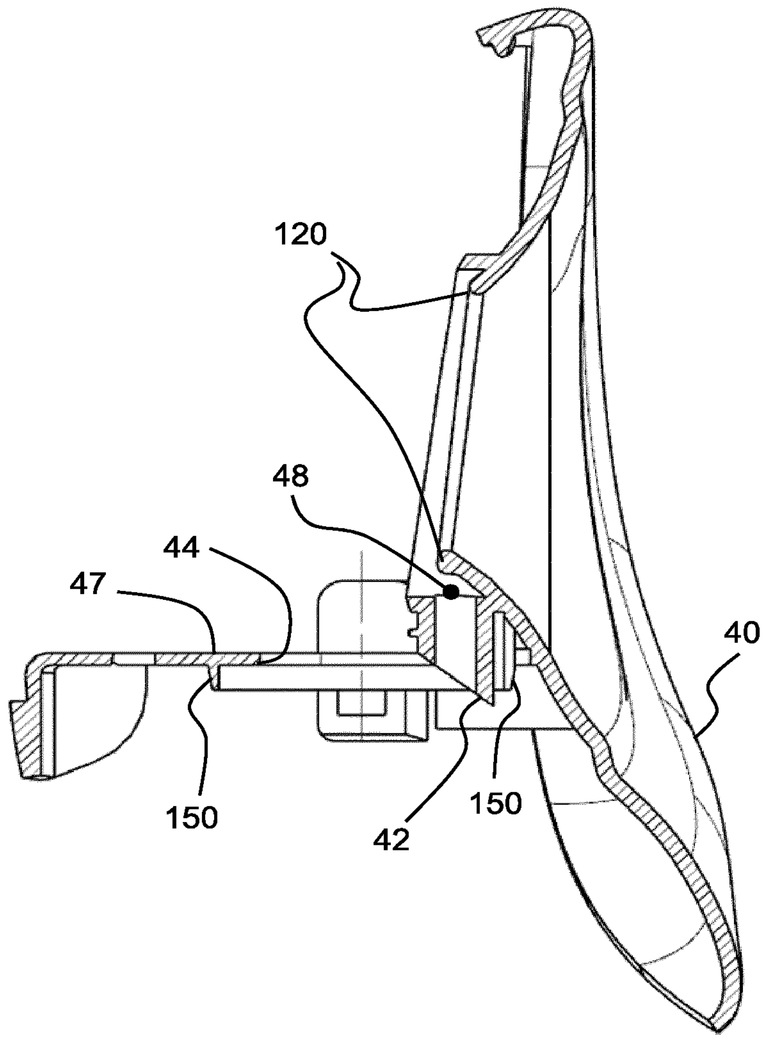
FIG. 15 shows the breast shield more clearly in cross section.

FIG. 15 shows the breast shield more clearly in cross section. A lip 150 extends down from the rim 47 to engage with the top of the container opening. This lip surrounds the rim opening 44.

The diaphragm is designed to deform in a predictable way in response to the applied under-pressure. It may for example be designed to implement a breast stimulation function.

The diaphragm of the invention may have a single fixed rotational orientation as explained above, meaning the flow paths can be designed to be more effective, based on their known orientation. There may however be a set of possible rotational orientations, for example there may be three possible orientations for a triangular design.

Various design features have been described above, in particular:

(i) The internal design of the cavity formed by the diaphragm, with the ridge which extends from a base of the cavity towards the center;

(ii) The angled back open end of the cavity formed by the diaphragm;

(iii) The diaphragm with integrated valve closure element and lid for sealing the opening through which the valve closure element is fitted; and (iv) The front and rear assemblies with the rear assembly having a release element which projects along channel in the front assembly.

These features are all independent design options with separate advantages and they may therefore be used in any combination.

In the examples above, the breast shield (in particular the frame) forms the valve seat. In other examples, the valve seat could be formed by the cover.

In the examples above, the tongue-simulation ridge extends from the open end of the cavity towards the closed end. It may also project forwards out of the cavity, i.e. towards the breast of the user.

In the examples above, the release actuator is at a front external surface of the front assembly. It may instead be at a side.

In the examples above, the diaphragm is connected to the breast shield and then held in place by the cover. In other designs, it may instead be fitted to the cover and then the cover and diaphragm may fit to the breast shield as a unit.

In the examples above, the milk container is directly attached to the remainder of the breast pump to form a wearable unit. Some of the design features may be applied to designs where the milk container is mounted somewhere else on the body, connected by a milk tube.

The breast pump described above has pump (typically of a motor and an impeller) a controller and a power source. Together these define a breast pump actuator and these are part of a wearable unit. However, some of the design features may be applied to designs where the breast pump actuator is located elsewhere on the body, connected by a pressure tube. The breast pump actuator may operate based on stimulation rather than mechanical pumping.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. An expression assembly for a breast pump comprising: a diaphragm; a breast shield to which the diaphragm is coupled, wherein the diaphragm is formed of a flexible membrane and comprises a cavity having an open end for receiving a nipple of a user and a closed end, wherein the open end has top and bottom parts which connect to the breast shield, wherein: the top part is set further back from the closed end in a direction parallel to a central forward outward axis of the diaphragm than the bottom part and a milk flow passage is defined at the bottom part of the open end.

2. The expression assembly of claim 1, further comprising a cover over the diaphragm to define a sealed space between them.

3. The expression assembly of claim 1, wherein the top part is set back by at least 10 mm further than the bottom part.

4. The expression assembly of claim 1, wherein the diaphragm further comprises a connecting portion which connects to the breast shield in a plane which, in a normal operating orientation of the expression assembly, is at an angle ($\alpha$) of between 10 and 20 degrees to the vertical.

5. The expression assembly of claim 1, wherein the diaphragm further comprises a valve closure element for forming part of a valve, the valve closure element extending from a bottom edge of the open end.

6. The expression assembly of claim 5, wherein the breast shield comprises a valve seat for supporting the valve closure element of the diaphragm to form the valve.

7. The expression assembly of claim 5, wherein the valve closure element is for controlling a flow path to a milk container through a first part of a container opening and the diaphragm further comprises a lid for closing a second part of the container opening.

8. The expression assembly of claim 7, wherein the breast shield defines a rim for engaging with the container opening, with a rim opening formed internally of the rim, wherein the valve closure element is for passing through the rim opening during fitting of the diaphragm to the breast shield and the lid is for closing the rim opening after fitting of the diaphragm to the breast shield.

9. The expression assembly of claim 1, wherein the cavity comprises a ridge which extends from a base of the cavity towards the center of the cavity.

10. The expression assembly of claim 9, wherein the diaphragm comprises a first side flow path to a first side of the ridge and a second side flow path to an opposite second side of the ridge.

11. The expression assembly of claim 9, wherein the diaphragm further comprises a second ridge which extends from a first side of cavity towards the center of the cavity, and a third ridge which extends from a second side of the cavity towards the center of the cavity.

12. The expression assembly of claim 1, wherein the flexible membrane has a non-uniform thickness with locally thinner regions to define hinge points.

13. The expression assembly of claim 12, wherein the flexible membrane has one of the hinge points at the back of the ridge.

14. A breast pump, comprising: the expression assembly of claim 1; a pressure source for delivering an under pressure to a sealed space; and a milk collection container.

* * * * *